United States Patent [19]

Zang

[11] Patent Number: 5,522,843
[45] Date of Patent: Jun. 4, 1996

[54] APPARATUS FOR ATTACHING SOFT TISSUE TO BONE

[75] Inventor: Kerry Zang, Paradise Valley, Ariz.

[73] Assignee: Orthopaedic Biosystems Limited, Inc., Scottsdale, Ariz.

[21] Appl. No.: 200,163

[22] Filed: Feb. 23, 1994

[51] Int. Cl.⁶ .................................................. A61B 17/00
[52] U.S. Cl. .............................................. 606/232; 606/73
[58] Field of Search .................................. 606/232, 220, 606/60, 72, 65–67, 73; 411/511; 623/13

[56] References Cited

U.S. PATENT DOCUMENTS

| 65,499 | 6/1867 | Miller . | |
|---|---|---|---|
| 3,910,281 | 10/1975 | Kletschka et al. . | |
| 4,738,255 | 4/1988 | Goble et al. . | |
| 4,741,330 | 5/1988 | Hayhurst . | |
| 4,776,328 | 10/1988 | Frey et al. . | |
| 4,988,351 | 1/1991 | Paulos et al. . | |
| 5,013,316 | 5/1991 | Goble et al. . | |
| 5,037,422 | 8/1991 | Hayhurst et al. . | |
| 5,100,417 | 3/1992 | Cerier et al. | 606/232 |
| 5,102,421 | 4/1992 | Anspach et al. . | |
| 5,120,171 | 6/1992 | Lasner | 606/73 |
| 5,129,902 | 7/1992 | Goble et al. . | |
| 5,152,790 | 10/1992 | Rosenberg et al. . | |
| 5,192,303 | 3/1993 | Gatturna et al. . | |
| 5,224,946 | 7/1993 | Hayhurst et al. | 606/232 |
| 5,336,240 | 8/1994 | Metzler et al. | 606/232 |
| 5,370,662 | 12/1994 | Stone et al. | 606/73 |

OTHER PUBLICATIONS

Fracture Appliances Brochure, Zimmer Co. Feb., 1947.

Primary Examiner—Stephen C. Pellegrino
Assistant Examiner—Jeffrey A. Schmidt
Attorney, Agent, or Firm—Michael K. Kelly; Snell & Wilmer

[57] ABSTRACT

A bone anchor for securing a suture to a bone comprising a head portion and a shaft. The head portion includes a flat head portion for impeding axial migration of the bone anchor into the bone and a dome portion having a tunnel for receiving a suture. The shaft secures the bone anchor to the bone. It extends from the head portion to a flat, distal end. The shaft includes a plurality of tine segments disposed in planes substantially perpendicular to the longitudinal axis of the bone anchor and a plurality of grooves extending along the shaft that divide each of the plurality of tine segments into a plurality of tines. Each of the plurality of tines has an upper surface substantially perpendicular to the longitudinal axis of the anchor, a frustroconical portion, and an arcuate junction defined by the intersection of the upper surface and the frustroconical portion. The angle of the arcuate junction for each of the plurality of tines at each of the tine segments increases along the length of the shaft from the head to the distal end.

20 Claims, 2 Drawing Sheets

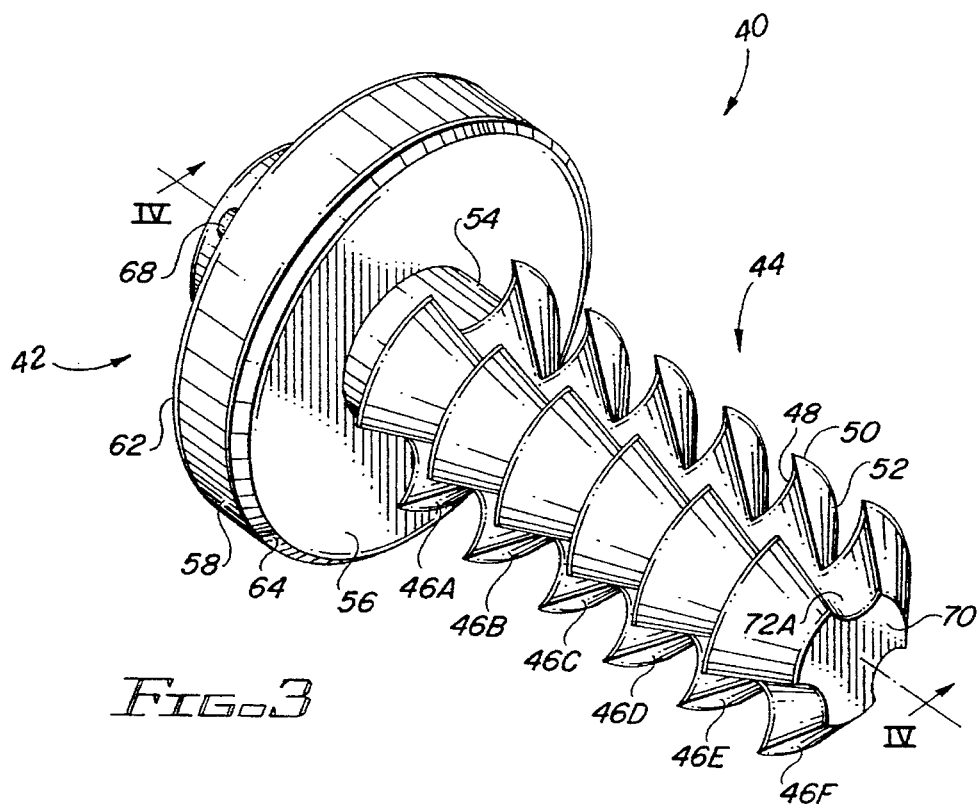
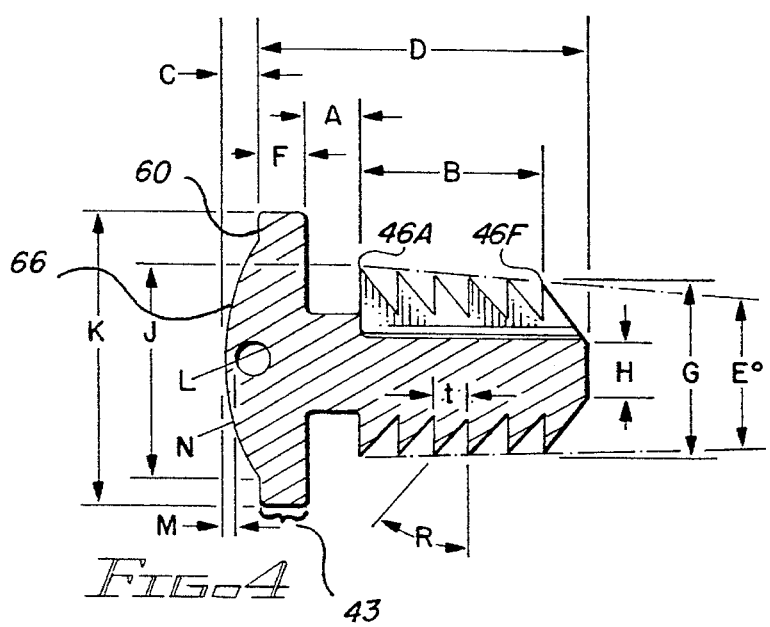
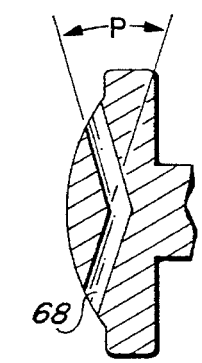
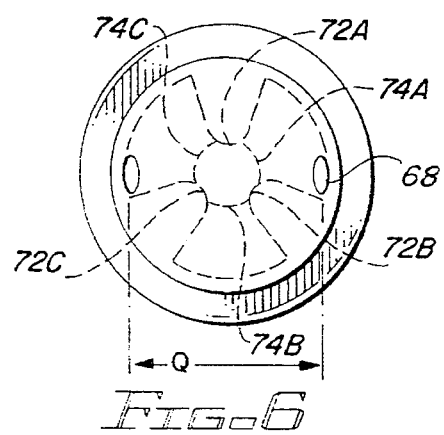

APPARATUS FOR ATTACHING SOFT TISSUE TO BONE

TECHNICAL FIELD

The present invention relates generally to apparatus for attaching soft tissue to bone, and more particularly to a bone anchor which functions as an attachment site for sutures used to retain soft tissue in intimate contact with a bone to permit reattachment of the soft tissue to the bone.

BACKGROUND ART AND TECHNICAL PROBLEMS

The principal components of a skeletal system, for example a human skeletal system, include bones which comprise the framework for the body, cartilage which forms the connecting and supporting structures among the bones, and ligaments which bind the bones together. When a ligament becomes detached from a bone, for example due to an athletic or other injury, it is often desirable to reattach the ligament to the bone.

Ligaments and other soft tissue (e.g., tendons) may be reattached to a bone in a number of different ways. For example, Goble et al. U.S. Pat. No. 5,013,316, issued May 7, 1991, discloses a soft tissue anchor comprising a footing stud that includes a drill and followed by self tapping threads, wherein the footing stud is arranged for turning and tapping into a bone mass. A longitudinal hole is disposed within the footing stud and is configured to receive and retain therein a tack which includes an undersurface comprising spikes for engaging and penetrating a ligament. When the tack is urged into the bore of the footing stud, the spikes engage the soft tissue and maintain it in intimate contact with the bone.

Goble et al. U.S. Pat. No. 4,738,255, issued Apr. 19, 1989, discloses a suture anchor system that includes a drill and guide arrangement for drilling an opening into a bone mass which is outwardly flared to accommodate a suture anchor dispensed from an applicator, which suture anchor is configured to be expanded within the bone mass to secure the anchor within the undersurface of the bone. As tension is applied to the suture, the anchor remains underneath the surface of the bone.

Hayhurst et al. U.S. Pat. No. 5,037,422, issued Aug. 6, 1991, discloses a bone anchor which comprises an elongated, thimble-shaped body having slots extending lengthwise through the body and a suture receiving opening provided in the tip of the body. At least one ridge or barb extends outwardly from the exterior of the body and defines an edge which is adapted to be lodged in the wall of a bore formed in the bone mass. The tip of the anchor is configured to be inserted into a bore in the bone, such that when tension is applied to the sutures, the resilient walls of the anchor are flared outwardly, locking the anchor into the bore within the bone.

Paulos et al. U.S. Pat. No. 4,988,351, issued Jan. 29, 1991, discloses a soft tissue washer for use with a bone screw for attaching soft tissue to a bone. The washer comprises a plurality of sharp pins extending from the distal face of the washer, there being a plurality of posts interposed among the pins also extending from the distal face of the washer. The washer comprises a central bore for receiving a bone screw therewithin. As the bone screw is tightened into the bone, the sharp pins engage the soft tissue to retain the tissue in intimate contact with the bone; the posts limit the degree of penetration of the pins into the bone such that the distal face of the washer is maintained a predetermined distance from the bone surface, such that the soft tissue is maintained between the distal face of the washer and the bone.

Anspach, Jr. U.S. Pat. No. 5,102,421, issued Apr. 7, 1992, discloses a suture anchor in the form of a rivet having three radially extended flanges configured for penetration into a bone. A cylindrical extension projects rearwardly from the flanges and has a suture secured thereto. A plurality of spiral grooves are formed within the flanges to facilitate turning of the anchor as it is tapped into a bone mass. The aforementioned grooves also serve to define a series of serrations therebetween, which serrations aid in preventing withdrawal of the anchor.

Other known devices attempt to dispose the suture anchor site wholly within or underneath the bone surface, such as the "Quick Anchor"™ bone anchor manufactured by Mitek Surgical Products, Inc. of Norwood, Mass. The Mitek Quick Anchor bone anchor is configured to be dropped within a bore of a bone mass using a collar device, functioning to retain expandable wings in a retracted position during insertion. Once the device is inserted into the bone cavity, the wings expand, much like a grappling hook, to prevent withdrawal of the device. Presently known suture anchor devices are unsatisfactory in several respects. For example, the suture attachment sites of many known devices are of sharp or otherwise irregular construction, tending to irritate adjacent tissue. Moreover, many known devices tend to migrate within the bone mass, which may result in the device becoming lodged within a joint. In addition, presently known devices require cumbersome tools and accessories for inserting the device, for example devices which require turning or screwing during insertion.

A suture anchor is thus needed which overcomes the short-comings of the prior art.

SUMMARY OF THE INVENTION

The present invention provides a suture anchor which addresses the shortcomings associated with the prior art.

In accordance with one aspect of the present invention, a bone anchor is provided which includes an elongated shaft having a flat head portion attached to a proximal end thereof. The head portion further comprises a rounded cap or dome which functions as a suture anchor site. During installation, the surgeon drills an elongated bore into the bone mass, and presses the shaft portion of the bone anchor into the bore. In accordance with a further aspect of the present invention, the bore includes a counterbore configured to receive the flat head portion of the anchor. The dome extending from the flat portion is suitably configured with openings through which sutures may be threaded, such that the sutures are securely anchored to the bone by the anchor device. The sutures may then be attached to soft tissue in a conventional manner.

In accordance with a further aspect of the present invention, the elongated shaft portion of the anchor device comprises a plurality of frustroconical tines which, when tension is applied to the sutures, tend to flare outwardly, locking the anchor in place and preventing outward migration of the device. Inward migration of the device is precluded by the engagement of the undersurface of the flat head portion of the device with the counterbore.

In accordance with yet a further aspect of the invention, the dome portion of the anchor device is suitably of integral construction with the head portion of the device, resulting in superior pullout strength of the device.

In accordance with yet a further aspect of the invention, the shaft portion of the anchor device comprises a plurality of lengthwise grooves extending along the length of the shaft resulting in a plurality of arcuate, spaced-apart tines extending along the length of the shaft. These grooves provide sites for bony ongrowth, further preventing axial and rotational migration of the device within the bone.

BRIEF DESCRIPTION OF THE DRAWING FIGURES

The subject invention will be hereinafter described in conjunction with the appended drawing figures, wherein like numerals designate like elements, and:

FIG. 3 is a side elevational view of an exemplary embodiment of the bone anchor device in accordance with the present invention;

FIG. 4 is a cross-section view of the bone anchor device of FIG. 3 taken along line IV—IV of FIG. 3;

FIG. 5 is a cross-section view of the head portion of the bone anchor device of FIGS. 3 and 4; and FIG. 6 is an end view of the anchor shown in FIG. 4, taken along line VI—VI of FIG. 4.

DETAILED DESCRIPTION OF PREFERRED EXEMPLARY EMBODIMENTS

Figure 1:
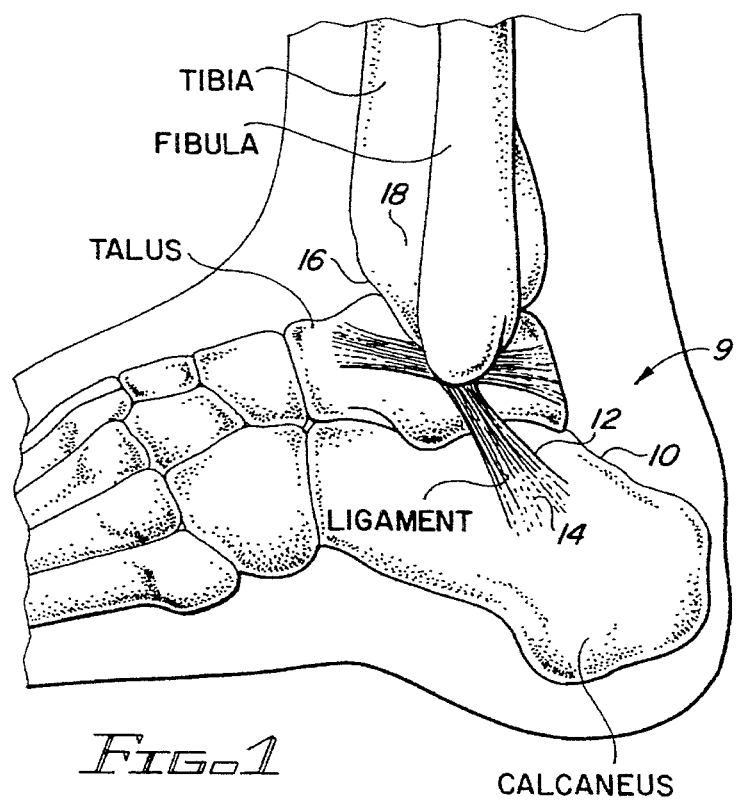
FIG. 1 is a schematic view of an anatomically normal human heel bone showing soft tissue properly attached to the bone.

Referring now to FIG. 1, a ligament 12 extends between a human tibia 16 and a human calcaneus bone (heel bone) 10 in an anatomically normal ankle joint. Ligament 12 is attached to tibia 16 at an attachment site 18, and attached to calcaneus 10 at an attachment site 14. Although attachment sites 14 and 18 appear to form an arcuate line in FIG. 1, those skilled in art will appreciate that soft tissues such as ligament 12 typically adheres to a bone over an irregular region which, for purposes of this discussion, is approximated by the arcuate attachment site shown in the Figure.

When soft tissue such as ligament 12 becomes detached from the bone, for example, as a result of an athletic injury or the like, it is often desirable to reattach the soft tissue to the bone. In this regard, it has become common practice to grasp the free (detached) end of the tissue with sutures, and to securely anchor the sutures to the bone proximate the reattachment site. If desired, the adjacent joint may be immobilized for a period of time to permit reattachment. With the soft tissue held in intimate contact with the bone, the tissue will naturally grow back into the bone surface, firmly reattaching itself to the bone in a relatively short period of time. For example, soft tissue 12 may begin reattaching itself to calcaneus 10 in a matter of twenty-one days, and will be substantially reattached to the point that the patient may walk on the ankle joint in as little as eight weeks. After approximately sixteen weeks, the reattachment process is substantially completed.

The natural physiological process whereby the soft tissue grows back into the bone occurs relatively quickly; hence, the useful life of the bone anchor device used to attach the suture to the bone proximate the reattachment site is thus on the order of sixteen weeks. However, because removal of the anchor device may require destruction of at least a portion of the reattached tissue, it is often desirable to simply permit the suture anchor to remain within the bone permanently. That being the case, it is highly desirable that the suture anchor exhibit a high pullout strength during the early stages of reattachment, and to exhibit a high resistance to migration thereafter. In addition, inasmuch as the suture anchor typically remains in situ permanently, it is desirable that the suture anchor be minimally intrusive; that is, the suture anchor advantageously comprises smooth, anatomically compatible surfaces exposed to adjacent tissue and bony structure.

Figures 2A, 2B, 2C:
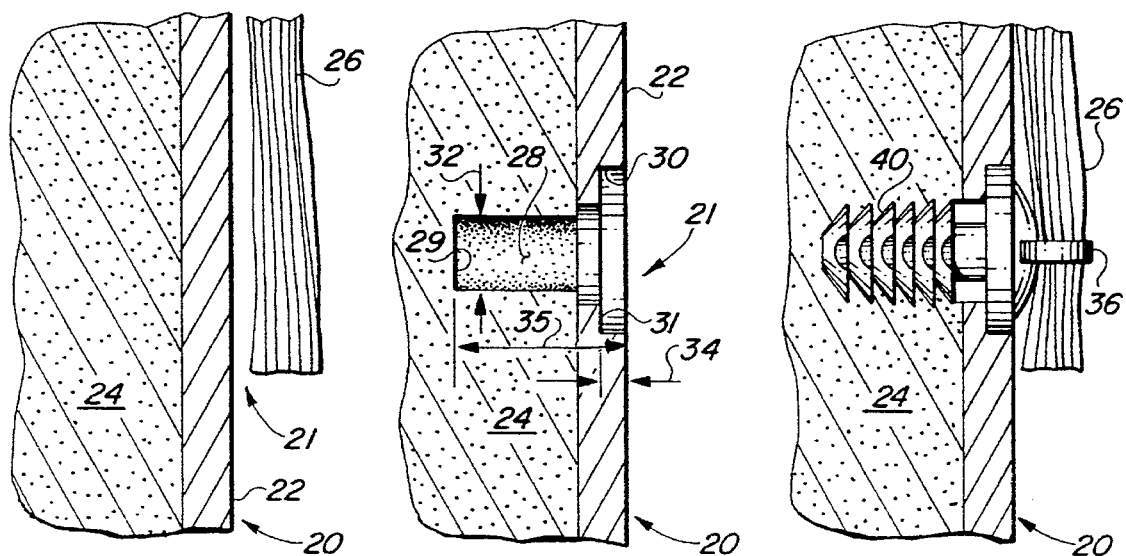
FIG. 2A is a schematic diagram of an exemplary flat bone anchor site showing soft tissue detached from the bone.
FIG. 2B is a schematic diagram of the bone anchor site of FIG. 2A shown prepared for receiving the bone anchor of the present invention.
FIG. 2C shows the bone anchor site of FIGS. 2A and 2B showing the subject bone anchor in situ, maintaining the reattached soft tissue in intimate contact with the bone.

Referring now to FIGS. 2A–2C, an exemplary soft tissue reattachment site 21 suitably comprises a bone 20 (for example analogous to calcaneus 10) and soft tissue 26 (for example analogous to ligament 12) which has become detached from bone 20. Those skilled in the art will appreciate that the structure of bone tissue is generally either compact, cortical bone, i.e., the hard, dense, outside layer of bone, or spongy (also referred to herein as cancellous bone), which contains many small cavities which may be filled with marrow. Moreover, bones are also generally classified according to their shape; that is, bones are either long (as in the bones of the extremities), short (for example, bones of the wrist, ankle, and sesamoid bones), or flat (such as bones of the cranium, scapula, and ribs). In addition, certain bones, for example bones of the vertebrae, are classified as irregular.

With continued reference to FIG. 2A, bone 20 may comprise a flat bone having an outer layer 22 of compact bone enclosing an inner-region 24 of cancellous bone.

Referring now to FIG. 2B, reattachment site 21 may be suitably prepared for reattachment of soft tissue 26 (not shown in FIG. 2B for clarity), by forming a bore 28 extending through outer layer 22 and into the cancellous portion 24 of bone 20. With momentary reference to FIG. 2C, an exemplary suture anchor device 40 may then be inserted into bore 28 to maintain soft tissue 26 in intimate contact with bone 20 to permit the soft tissue to naturally reattach itself to the bone.

Referring now to FIG. 3, suture anchor 40 suitably comprises a shaft portion 44, a head portion 42, and a neck portion 54 interposed therebetween. Neck portion 54 is suitably integral with head portion 42, and in a preferred exemplary embodiment, is substantially cylindrical in shape.

Head portion 42 suitably comprises a disc portion 43 and a dome 66 extending therefrom. Dome 66 advantageously includes one or more suture tunnels 68, as described in greater detail below in conjunction with FIGS. 5 and 6.

Disc portion 43 further comprises a substantially flat, annular, undersurface 56 and a substantially flat, annular upper surface 60 separated by a circumferential land 58. In accordance with a preferred exemplary embodiment, disc portion 43 suitably comprises a first beveled surface 62 joining land 58 and upper surface 60, and a second bevelled surface 64 joining land 58 and undersurface 56.

With continued reference to FIG. 3, shaft portion 44 suitably comprises a plurality of frustroconical tines 46A–46F. In the illustrated embodiment, shaft portion 44 suitably comprises six (6) tine segments, namely, respective segments 46A–46F. However, any suitable number of tine portions may be employed in the context of the present invention, for example in the range of one to twelve or more, depending on the particular bone mass within which the device is to be installed, and most preferably on the order of four to eight tine portions.

In accordance with a further aspect of the invention, respective tine portions 46A–46F each comprise a flat annular surface 48 disposed in a plane substantially perpendicular to the longitudinal axis of anchor 40, an angled, frustroconical portion 52, and an arcuate junction 50 defining the junction between flat portion 48 and angled portion 52. Shaft portion 44 suitably terminates at a flat, distal land 70.

With continued reference to FIG. 3 and as discussed in greater detail below in conjunction with FIG. 6, shaft portion 44 suitably comprises one or more grooves 72 extending along the length of shaft portion 44.

More particularly and with reference to FIGS. 3 and 6, respective grooves 72A, 72B, and 72C are suitably spaced apart along shaft 44, forming respective tine sections 74A, 74B, and 74C. As best seen in FIG. 3, each of respective tine sections 74A–74C comprises a portion of respective tine segments 46A–46F. Although respective grooves 72A–72C are substantially semicircular in cross section as shown in FIG. 6, virtually any geometry may be employed such that respective tine sections 74A–74C are spaced apart from one another. In this way, when anchor 40 is installed within a bone mass, bony ingrowth may penetrate the interstices formed by respective grooves 72A–72C intermediate tine segments 74A–74C. The presence of this bony ingrowth helps ensure that anchor 40 remains stationary within the bony mass. In particular, the presence of bony ingrowth within respective grooves 72A–72C substantially impedes rotational migration of anchor 40, as well as substantially impeding axial migration (either into the bone or out of the bone) by enveloping the complex geometric structure comprising shaft 44.

Referring now to FIGS. 4–6, the outer diameter of shaft 44 may be substantially constant along its length in accordance with a first embodiment of the invention (not shown). In the alternate preferred embodiment shown in FIG. 4, the outer diameter of the tines suitable decreases, for example linearly, from tine segment 46A to tine segment 46F.

More particularly, the diameter of shaft 44 may decrease along its length approaching land 70, such that an included angle E defined by the convergence of the shaft diameter is suitably on the order of 0–10 degrees or more, and preferably in the range of 5–6 degrees, and most preferably on the order of six degrees. In the illustrated embodiment wherein each respective tine segment 46A–46F is suitably substantially equal in length, i.e., wherein each tine segment has an approximately equal axial dimension, the various angles defined by junction 50 increase from tine segment 46A to tine segment 46F, that is, each respective land 48 corresponding to tine segments 46A–46F decreases along the length of shaft 44 (to the left in FIG. 4), each angled segment 52 also decreases along the length of shaft 44, and the angle defined by junction 50 for each tine segment correspondingly increases along the length of shaft 44 (i.e., from right to left in FIG. 4). In this regard, while the respective angled junctions 50 corresponding to the various tine segments are shown as a sharp corner in the drawing Figures, it may be advantageous from a manufacturing standpoint to include a small radius at junction 50 in lieu of a sharp corner.

With continued reference to FIG. 4, an internal angle R may also be defined for each tine segment. Consistent with the foregoing discussion, the angle R for each tine segment will increase along the length of shaft 44 (i.e., from right to left in FIG. 4).

In a preferred embodiment of the invention, an axial dimension t, for example, a common dimension for each respective tine segment 46A–46F, may be defined as shown in FIG. 4. In a particularly preferred embodiment, axial dimension t for each tine segment is suitably on the order of 0.025–0.040 inch, and most preferably on the order of about 0.030 inch, such that the length of shaft 44 for the 6 tine embodiment shown in the Figures is on the order of approximately 0.180 inch. In particular, the length of shaft 44 is most desirably approximately 0.120 inch for use in conjunction with small bones or for use with small children, and may suitably be on the order of 0.240 inch for use in middle sized bones or in average sized people, and approximately 0.360 inch for large bones and/or for use in larger individuals.

While any desired angle E may be employed in the context of the present invention, an angle on the order of five degrees facilitates convenient insertion and self-alignment of anchor 40 into bore 28, as discussed in greater detail below.

With continued reference to FIG. 2 and 4–6, a surgeon suitably prepares a reattachment site 21 in the following manner.

With particular reference to FIG. 2B, a bone drill (not shown) is suitably employed to introduce bore 28 in the bone site, which extends through compact layer 22 and cancellous layer 24. The total length of bore 28, i.e., from the outer surface of compact layer 22 until the bottom 29 of bore 28, is referred to in FIG. 2B as dimension 35. With momentary reference to FIG. 4, dimension 35 (FIG. 2B) corresponds to dimension D of anchor 40, and is advantageously in the range of 0.20 inch to 0.50 inch, and most preferably in the range of 0.33 inch to 0.45 inch. In practice, it may be desirable for dimension 35 of bore 28 (FIG. 2B) to exceed dimension D of anchor 40 (FIG. 4) by a small amount, for example on the order of 0.001 to 0.020 inch. In this way, disc portion 43 of head 42 is advantageously disposed beneath the surface of compact bone layer 22 when anchor 40 is installed.

With continued reference to FIG. 2B, a counterbore 30 is suitably created in compact layer 22, either by using the same drill employed to create bore 28 or by using a secondary tool in addition to or in conjunction with the drill used to create bore 28. In order to maintain proper alignment, counterbore 30 and bore 28 are desirably created using a single tool (not shown). With momentary reference to FIGS. 2B, 3, and 4, the axial dimension of counterbore 30 is suitably equal to or slightly greater than the thickness of disc 43 (corresponding to dimension F in FIG. 4), and is suitably on the order of 0.020 to 0.50 inch, and most preferably on the order of about 0.40 inch. The depth of counterbore 30 is limited by the thickness of compact bone layer 22 in the vicinity of the reattachment site, and, hence, the size of anchor 40 is advantageously selected in accordance with the physical dimensions of the reattachment site.

In any event, the depth of bore 28 should be selected so that undersurface 56 of disc 43 engages corresponding surface 31 of counterbore 30; that is, while base 70 of device 40 should desirably be proximate base 29 of bore 28 when anchor 40 is installed, it is not necessary that base 70 of device 40 contact base 29 of bore 28, whereas it is highly desirably that undersurface 56 of device 40 physically engage surface 31 of counterbore 30. In this way, inward axial migration of anchor 40 will be substantially inhibited to the extent the integrity of compact bone layer 22 in the vicinity of counterbore 30 remains intact.

The diameter of bore 28 should be selected to be equal to or slightly smaller than the largest diameter of respective tine segments 46A–46F. More particularly, the diameter of bore 28, illustrated as dimension 32 in FIG. 2B, is advantageously on the order of 0.010 to 0.040 (and most preferably on the order of 0.028 inch) smaller than dimension G (see FIG. 4) of device 40. In this way, the various arcuate junctions 50 corresponding to the tine segments will frictionally engage the circumferential walls of bore 28 during insertion of anchor 40 into device 28. Depending on various physical characteristics of the material comprising anchor 40 as discussed in greater detail below, and further depending on the hardness of the bone and the vicinity of reattachment site 21, and further depending on the physical dimensions of the various tine segments in the vicinity of respective junctions 50, the frictional engagement between shaft 44 and bore 28 may result in a deflection of the tine segments as the device is inserted into the bore, the deflection of compact bone 22 and cancellous bone 24 proximate the device, or a combination of both. To the extent anchor 40 frictionally engages the bone during insertion, the outward flaring of respective tine segments 46A–46F (and particularly in the region of respective arcuate junctions 50) with respect to the bone proximate thereto will inhibit outward axial migration of anchor 40.

Finally, the diameter of counterbore 30 should advantageously be approximately equal to or slightly greater than the diameter of disc 43 (dimension L in FIG. 4). In the preferred exemplary embodiment shown in the drawing Figures, dimension L is suitably on the order of 0.020 to 0.10 inch, and most particularly on the order of 0.040 to 0.075 inch, and most preferably on the order of about 0.0625 inch. Thus, the diameter of counterbore 30 should suitably be on the order of 0.000 to 0.030 inch, and most preferably on the order of 0.020 inch, greater than dimension L to facilitate optimum seating of device 40 within counterbore 30.

With continued reference to FIGS. 2B and 2C, after reattachment site 21 is properly prepared by the surgeon, anchor 40 may be suitably inserted into bore 28, for example by urging the device into the bore by pressure exerted by the surgeon's thumb or forefinger, or by tapping the device with a suitable impact tool. When anchor 40 is firmly seated within the bore, soft tissue 26 may be suitably secured to the attachment site with one or more sutures 36, as is known in the art. In this regard, sutures 36 may be threaded through tunnel 68 prior to inserting anchor 40 into the bore, after the anchor is partially seated within the bore, or upon fully seating the anchor within the bore.

More particularly and with reference to FIGS. 5 and 6, the cross-sectional area of tunnel 68 is suitably large enough to accommodate one or more sutures extending through the tunnel. It is also desirable to ensure that sufficient material is present within dome 66 to avoid breakage even as substantial tension is applied to the sutures, for example during attachment of the soft tissue. Moreover, the cross-sectional area of tunnel 68 should also be sufficient to permit standard suture needles to conveniently pass through the tunnel, even when device 40 is seated within a bone.

To facilitate the convenient threading of sutures through anchor 40 in situ, an included angle P associated with tunnel 68 may be defined, which is suitably on the order of 10–60 degrees, and preferably on the order of 25–35 degrees, and most preferably about 30.6 degrees. Furthermore, the distance between the respective openings comprising tunnel 68 may be conveniently defined as dimension Q (FIG. 6), suitably on the order of 0.030 to 0.090 inch, and preferably on the order of 0.050 to 0.075 inch, and most preferably about 0.060 inch. Finally, the diameter of tunnel 60 is suitably on the order of 0.020 to 0.060 inch, and most preferably about 0.045 inch.

Once anchor 40 is installed within the bone site, for example as shown in FIG. 2C, and soft tissue 26 is suitably reattached to the bone site via sutures 36, it is desirable to minimize irritation of soft tissue 26 and surrounding tissue by device 40. In this regard, it is desirable to seat disc 43 within counterbore 30 to the extent permitted by the anatomical configuration of bone site 21. In addition, it is desirable that the geometry of dome 66 be such as to minimize discomfort associated with the contact between dome 66 and the adjacent anatomy.

More particularly, dome 66 is suitably highly polished, and exhibits a smooth, curved surface, for example a hyperbolic, ellipsoid, or semispherical shape. In addition, the respective openings comprising tunnel 68 may be radiused, bevelled, or otherwise configured to avoid sharp corners. In a particularly conferred embodiment, dome 66 suitably comprises a substantially uniform radius on the order of 0.100 to 0.176 inch, and most preferably on the order of 0.130 inch resulting in a maximum dimension C (FIG. 4) on the order of 0.020 to 0.070 inch, and most preferably about 0.050 inch.

For reattachment sites such as that shown in FIG. 2, i.e., wherein a substantially flat bone surface is available, disc 43 may be substantially seated within counterbore 30. However, it may also be desirable to employ anchor 40 at reattachment sites which are either concave, convex or otherwise irregular. Accordingly, the diameter and thickness of disc 43, as well as various other dimensions of head 42 (in particular the dome 66) may be configured to provide adequate material strength to avoid breakage as tension is applied to the sutures, while at the same time providing smooth, nonabrasive and minimally invasive surfaces to reduce irritation of surrounding tissue.

In accordance with a further aspect of the present invention, anchor device 40 is advantageously made from any suitable biocompatible material, for example titanium alloy, stainless steel, class six implant grade plastic, and the like, or any other biocompatible material which exhibits adequate pullout strength, sufficient strength to avoid breakage as the sutures are pulled, and having sufficiently low brittleness to avoid breakage during long term usage of the device in situ. Alternatively, in view of the relatively short useful life of device 40 (as discussed above), device 40 may be made from a suitable bioabsorbable material, for example, polyglycolic acid, a material distributed by Johnson & Johnson under the name ORTHOSORB™.

In accordance with a further aspect of the invention, shaft 44 and, if desired, neck portion 54 and at least underside 56 of disc 43 may suitable exhibit a course finish to further promote bony ingrowth and thereby further stabilize anchor 40 against any degree of migration.

Although the subject invention has been described herein in conjunction with the appended Figures, those skilled in the art will appreciate that the scope of the invention is not so limited. Various modifications in the arrangement of the components discussed and the steps described herein for using the subject device, may be made without departing from the spirit and scope of the invention as set forth in the appended claims.

I claim:

1. An anchor for reattaching soft tissue to a bone, comprising:

a head disposed at a proximal end of said anchor, including a dome portion having a channel disposed thereon for receiving sutures, said channel being configured such that said sutures extend in the direction of said proximal end when engaging soft tissue; and an integral shaft portion immovably affixed to and extending from said head portion and terminating at a distal end opposite from said proximal end, said shaft portion including at least two circumferentially spaced apart grooves defining at least two circumferentially spaced apart tine sections extending along at least a portion of the length of said shaft, each of said tine sections comprising a plurality of resiliently deformable tines spaced apart along at least a portion of the length of said shaft.

2. The anchor of claim 1 wherein each of said tines comprises an upper surface disposed in a plane substantially perpendicular to a longitudinal axis of said anchor, a frustroconical portion, and an arcuate junction defined by the intersection of said upper surface and said frustroconical portion; and further wherein the distance from said longitudinal axis to said arcuate junction for each of said tines decreases along the length of said shaft portion from said head to said distal end.

3. The anchor of claim 2 wherein said distance decreases linearly along said shaft portion, resulting in an angle of approximately zero to ten degrees between said axis and an imaginary line connecting said respective arcuate junctions.

4. The anchor of claim 1 wherein said anchor further includes a flathead portion disposed at the junction between said dome portion and said shaft portion, said flathead portion being integral with said dome portion and having a diameter larger than said shaft portion for impeding axial migration of said anchor into said bone.

5. The anchor of claim 4 wherein said flathead portion includes a substantially flat, annular undersurface, a substantially flat, annular upper surface, and a circumferential land extending therebetween, and wherein a first beveled surface joins said circumferential land and said upper surface and a second beveled surface joins said circumferential land and said undersurface.

6. The anchor of claim 4 wherein said flathead portion has a diameter in the range of 0.020 to 0.10 inches.

7. The anchor of claim 1 wherein each of said tines has an upper surface disposed in a plane substantially perpendicular to a longitudinal axis of said anchor, a frustroconical portion, and an arcuate junction defined by the intersection of said upper surface and said frustroconical portion; and wherein the angle between said upper surface and said frustroconical portion for each of said tines increases along the length of said shaft portion from said head to said distal end.

8. The anchor of claim 7 wherein each of said tine sections comprises one to twelve axially adjacent tines having an axial spacing in the range of 0.025 to 0.040 inches.

9. The anchor of claim 8 wherein said shaft portion has a length on the order of 0.180 to 0.360 inches, and wherein said distal end is substantially flat.

10. The anchor of claim 1 wherein said channel comprises at least two channel segments intersecting in said head so as to form an angle in the range of 120 to 170 degrees.

11. The anchor of claim 10 wherein each of said channel segments exhibits a length in the range of 0.030 to 0.090 inches and a diameter in the range of 0.020 to 0.060 inches.

12. The anchor of claim 1 wherein said dome portion exhibits a radius of curvature of approximately 0.100 to 0.176 inches and a thickness on the order of 0.020 to 0.070 inches.

13. The anchor of claim 1 made of a material from the group consisting of titanium alloy, stainless steel, class six implant grade plastic, and polyglycolic acid.

14. A bone anchor for securing a suture to a bone and having a longitudinal axis, comprising:

a head including a dome portion having a tunnel for receiving a suture; and a shaft portion extending from said head portion to a distal end, said shaft portion including a plurality of tine segments each having an upper surface disposed in a plane substantially perpendicular to said longitudinal axis, and a plurality of grooves extending along said shaft portion and dividing each of said plurality of tine segments into a plurality of tines;

wherein each of said tines comprises said upper surface substantially perpendicular to said longitudinal axis, a frustroconical portion, and an arcuate junction defined by the intersection of said upper surface and said frustroconical portion, wherein the angle between said upper surface and said frustroconical portion for each of said tines increases along the length of said shaft from said head to said distal end.

15. The bone anchor of claim 14 wherein the distance from said longitudinal axis to said arcuate junction for each of said plurality of tines decreases along the length of said shaft portion from said head to said distal end.

16. The bone anchor of claim 14 further including a flathead portion between said dome portion and said shaft portion, said flathead portion being integrally connected to said dome portion and having a diameter larger than the diameter of said shaft portion for impeding axial migration of said bone anchor into said bone.

17. The bone anchor of claim 16 wherein said flathead portion includes a substantially flat, annular undersurface, a substantially flat, annular upper surface, and a circumferential land and wherein a first beveled surface joins said circumferential land and said upper surface and a second beveled surface joins said circumferential land and said undersurface.

18. The bone anchor of claim 17 wherein said tunnel of said dome portion has at least two openings, said at least two openings intersecting in said head at said longitudinal axis so as to form an angle in the range of 120 to 170 degrees.

19. The bone anchor of claim 18 wherein said plurality of grooves extending along said shaft portion have a semicircular configuration.

20. A method for reattaching soft tissue to a bone comprising:

forming a bore having a first diameter in said bone, said bore extending through a compact layer of said bone into a cancellous layer of said bone;

forming a counterbore having a second diameter at the surface of said compact layer, said counterbore being coupled with said bore and said second diameter of said counterbore being greater than said first diameter; and inserting an anchor into said bore and said counterbore, said anchor comprising a head including a flat head portion for impeding axial migration of said bone anchor into said bone and a dome portion having a tunnel for receiving a suture, and a shaft portion for securing said bone anchor to said bone, said shaft portion extending from said head portion to a distal end and including a plurality of tine segments disposed in planes substantially perpendicular to a longitudinal axis of said bone anchor and including a plurality of grooves extending along said shaft portion and dividing each of said plurality of tine segments into a plurality of tines, each of said plurality of tines having an upper surface substantially perpendicular to said longitudinal axis of said anchor, a frustroconical portion, and an arcuate junction defined by the intersection of said upper surface and said frustroconical portion, and wherein the angle of said arcuate junction for each of said plurality of tines at each of said tine segments increases along the length of said shaft portion from said head to said distal end.

* * * * *